United States Patent [19]

Foltz et al.

[11] Patent Number: 6,094,591
[45] Date of Patent: Jul. 25, 2000

[54] MEASUREMENT OF CORONARY FLOW RESERVE WITH MR OXIMETRY

[75] Inventors: Warren D. Foltz, St. John's Newfoundland; Naeem Merchant; Graham A. Wright, both of Toronto, all of Canada

[73] Assignee: Sunnybrook Health Science Centre, Toronto, Canada

[21] Appl. No.: 09/058,342

[22] Filed: Apr. 10, 1998

[51] Int. Cl.[7] .................................................. A61B 5/055
[52] U.S. Cl. .......................................... 600/419; 324/306
[58] Field of Search .................................. 600/410, 419; 324/306, 307, 309

[56] References Cited

U.S. PATENT DOCUMENTS

| 5,070,877 | 12/1991 | Mohiuluddin et al. | 600/410 |
| 5,408,180 | 4/1995 | Mistretta et al. | 324/306 |

OTHER PUBLICATIONS

Estimating Oxygen Saturation of Blood in Vivo with MR Imaging at 1.5T, JMRI 1991; 1:275–283, Graham A. Wright, et al.

$T_2$ Accuracy on a Whole–Body Imager, MRM 38: 759–768 (1997), W D. Foltz, et al.

What is the Optimum Phased Array Coil Design for Cardiac and Torso Magnetic Resonance?, MRM 37:591–599 (1997), Paul A. Bottomley, et al.

Coronary Angiography with Magnetization–prepared $T_2$ Contrast, MRM 33:696–696 (1995), Jean H. Brittain, et al.

Partial Volume Effects on Vascular $T_2$ Measurements, Dept. Of Med. Biophysics, Sunnybrook Health Science Ctr, Toronto Ontario Canada, J.A. Stainsby, et al.

Effect of Coronary Artery Occlusion on Regional Arterial and Venous $O_2$ Saturation, $O_2$ Extraction, Blood Flow, and $O_2$ Consumption in the Dog Heart, Dept. Of Physiology and Biophysics, College of Medicine & Dentistry of NJ, vol. 47, No, Sep. 1980, Harvey R. Weiss.

Maximal coronary flow and the concept of coronary vascular reserve, Circulation, Aug. 1984, vol. 70/No. 2, 153–159, Julien I.E. Hoffman, M.D.

Simultaneous Measurement of Coronary Venous Blood Flow and Oxygen Saturation During Transient Alternation in Myocardial Oxygen Supply and Demand, American Journal of Cardiology, Mar. 1992, vol. 49, pp. 743–752, Baim, et al.

Cardiac Catherization and Angiography, Evaluation of Myocardial Blood Flow and Metabolism, 1986, pp. 328—332, Lea and Febiger.

Coronary vascular reserve in humans: a critical review of methods of evaluation and of interpretation of the results, European Heart Journal (1995), 16 (Supp. 1), 7–21, Nitenberg, et al.

Initial Studies of MR Oximetry in Patients with Congenital Heart Defects, Kim et al, Sunnybrook Health Science Centre, Canada.

Partial Volume Effects on Vascular T2 Measurement, Stainsby, et al., Sunnybrook Health Science Centre, Canada.

Error Analysis for MR Oximetry In Vivo, Wright, et al. Dept. Of Elec. Eng., Rad., Surg., Int. Med., Stanford Univ. Stanford CA.

Flow Insensitive Vascular $T_2$ Measurement, Foltz, et al., Dept. Of Med. Biophysics, Univ. Of Toronto & Sunnybrook Health Science Centre, Canada.

Improved Vascular T2 Measurements around the Heart Using Respiratory Compensation, Stainsby, et al., Dept. Of Med. Biophysics, Univ. Of Toronto, Dept. Of Ele. Eng., Stanford Univ., Stanford CA.

*Primary Examiner*—Brian L. Casler
*Attorney, Agent, or Firm*—Quarles & Brady; Christian G. Cabou; Phyllis Y. Price

[57] ABSTRACT

An MR oximetry measurement of % $O_2$ employs a pulse sequence comprised of a $T_2$ preparatory segment and an image data acquisition segment. The pulse sequence is used in methods for measuring coronary flow reserve and for measuring myocardial oxygen consumption.

8 Claims, 5 Drawing Sheets

FIG. 5

MEASUREMENT OF CORONARY FLOW RESERVE WITH MR OXIMETRY

BACKGROUND OF THE INVENTION

The field of the invention is nuclear magnetic resonance (MR) methods and systems. More particularly, the invention relates to the measurement of $T_2$ in vascular blood and the use of that measurement to determine coronary flow reserve.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, and this signal may be received and processed to form an image or to measure characteristics of the excited spins.

One characteristic of the spins that can be measured using MR is the $T_2$ constant. When the $B_1$ excitation signal is removed, an oscillating sine wave is induced in a receiving coil by the rotating field produced by the transverse magnetic moment $M_t$. The frequency of this signal is the Larmor frequency, and its initial amplitude, $A_0$, is determined by the magnitude of $M_t$.

The amplitude A of the emission signal (in simple systems) decays in an exponential fashion with time, t:

$$A = A_0 e^{-1/T_2}$$

The decay constant $1/T_2$ is a characteristic of the process and it provides valuable information about the substance under study. The time constant $T_2$ is referred to as the "spin-spin relaxation" constant, or the "transverse relaxation" constant, and it measures the rate at which the aligned precession of the nuclei dephase after removal of the excitation signal $B_1$.

It is well known that the $T_2$ time constant of blood is determined in part by the degree to which the hemoglobin is oxygenated. As reported by G. A. Wright et al., "Estimating Oxygen Saturation of Blood in Vivo with MR Imaging at 1.5 T", *JMRI* 1991; 1:275–283, the percentage of hemoglobin that is oxygenated (% $O_2$) can be quantitatively measured using a series of $T_2$-weighted MR images. This MR oximetry method works well when measuring blood oxygenation in large vessels that have little motion and that are positioned to produce high SNR images. The MR oximetry method does not work well, however, on small centrally located vessels, such as the coronary veins that drains the heart and vessels that have considerable motion.

Coronary flow reserve is defined as the ratio between the peak and basal coronary blood flows at the same perfusion pressure ($Q_{peak}/Q_{basal}$) The coronary flow reserve is a characteristic measurement of global coronary function, and it is decreased in people with significant coronary artery disease. Measurement of the coronary flow reserve provides valuable diagnostic information to the physician.

Quantitative and non-invasive methods to assess coronary flow reserve do not exist at present. Current methods rely on the imaging of pharmaceuticals to visualize qualitative changes in myocardial perfusion. Direct measurements of coronary flow reserve using Doppler ultrasound and MR methods are difficult to perform due to technical challenges and the complexities of the in vivo environment. The development of a flow reserve measurement which is both quantitative and non-invasive could significantly impact patient management and treatment planning for ischemic heart disease.

SUMMARY OF THE INVENTION

The present invention is a method for measuring blood oxygen saturation (% $O_2$) using magnetic resonance imaging. Using this MR oximetry method, the coronary flow reserve and myocardial oxygen consumption can be measured non-invasively. Based on the Fick Law, coronary flow is inversely proportional to the difference in % $O_2$ between the aorta and the draining coronary vein. One vein of particular interest is the coronary sinus. According to the present invention the $Q_{peak}$ and $Q_{basal}$ are determined via oximetry measurements before and after drug-induced coronary vasodilation. Aortic % $O_2$ is measured in the periphery using a known pulsed oximeter and sinus vein % $O_2$ is measured using the improved MR oximetry method.

One aspect of the invention is a coronary sinus MR oximetry measurement method and its application to measurements of coronary flow reserve. Relative to MR oximetry in the great vessels, sinus MR oximetry is particularly difficult due to the sinus' reduced size (~8–10 mm diameter), central location, and low blood oxygenation (% $O_2$~30%). These characteristics combine to limit the SNR available when using large vessel MR oximetry techniques. The present invention addresses these challenges through the use of a phase array cardiac receiver coil in the data acquisition method and through the use of an improved MR oximetry pulse sequence. As a result of these improvements, coronary sinus blood signal can now be imaged with sufficient SNR and spatial resolution for high fidelity oximetry.

GENERAL DESCRIPTION OF THE INVENTION

MR oximetry relies on a physical measurement of vascular $T_2$, a mathematical model and calibration to relate $T_2$ to % $O_2$, and a measurement protocol. As disclosed in U.S. Pat. No. 5,233,991 which is incorporated herein by reference, the prior art measurement is performed using a pulse sequence which was specially designed for measurements of vascular $T_2$. A $90_x$ excitation pulse is followed by a train of $180_y$ refocusing pulses, which are equally separated by a refocusing interval termed $\tau_{180}$. Spatial localization is performed using a final slice-selective pulse followed by an imaging gradient. To measure $T_2$, a series of $T_2$-weighted images is acquired with this pulse sequence in which the duration of the refocusing train is set to different values by changing the number of refocusing pulses used. With these images, $T_2$ of blood can be estimated by extracting the signal amplitude within the blood vessel and fitting the data points as a monoexponential decay using a weighted least squares fit.

To minimize flow sensitivity when using this pulse sequence, the excitation pulse and refocusing train are non-selective. Thus, there are no gradients applied and no moments to be nulled. In addition, the regular refocusing achieved by the train of $180_y$ pulses lessens the amount of dephasing due to flow through susceptibility gradients. Assuming ideal RF homogeneity, phase accrued by spins moving at a constant velocity through local $B_0$ inhomogeneity can be modeled as a linear gradient. The validity of such a model improves as $\tau_{180}$ decreases because spins travel a shorter distance between pulses. The prior art method used a $\tau_{180}$ interval of 24 ms.

The measured $T_2$ values are related to blood oxygen saturation using a mathematical model and calibration. The mathematical model, which is a simplified form of the Luz-Meiboom model of relaxation due to exchange between two sites at different frequencies, is described in the following equation:

$$\frac{1}{T_2} = \frac{1}{T_{2,0}} + K(\tau_{180}, \omega_0) * (1 - \%HbO2/100\%)^2 \quad (1)$$

where $T_{2,0}$ is the spin-spin relaxation time of fully oxygenated blood, $\omega_o$ is the resonant nuclei frequency, and K is a constant. The parameters $T_{2,0}$ and K are determined using an in vitro calibration. Details of the calibration are disclosed in U.S. Pat. No. 5,322,991.

One aspect of the present invention is the implementation of a $T_2$-weighted magnetization preparation segment as part of the MR oximetry pulse sequence. With this modification, the $T_2$-weighted magnetization produced by the train of $180_y$ refocusing pulses is returned to the longitudinal axis at the echo of the final refocusing pulse, instead of remaining within the transverse plane as in the prior art. Manipulation of $T_2$ contrast from the transverse plane back to the longitudinal axis is achieved using a $90_{-x}$ tip-up pulse. At this time, a spoiler gradient is also applied along the slice-select axis to dephase any residual transverse magnetization.

The principal advantage of temporary longitudinal storage of $T_2$ contrast using the present invention is the flexibility it allows in the choice of imaging pulse sequences. For example, in one embodiment the $T_2$ preparation segment is followed by an imaging pulse sequence in which a series of tip-up angle RF excitations follow the tip-up RF pulse at the completion of the $T_2$ preparation segment. Different slices or different part of k-space may be acquired after each small tip angle RF excitation pulse. In the preferred embodiment described below, a single slice imaging pulse sequence is used in which a spectrally and spatially selective RF excitation pulse and spiral interleaf readout is employed. Because the spectral-spatial RF pulse selectively excites water while isolating the slice of interest, this sequence rejects lipids. The spiral acquisition is well-suited for vascular imaging due to its good flow properties.

In addition to tipping the $T_2$-weighted magnetization back into the longitudinal axis, a number of improvements are made to the $T_2$ preparation segment. The effects of RF and static field inhomogeneities during the refocusing train are addressed using trains of relatively simple composite refocusing pulses with good RF cycling patterns. The preferred embodiment uses a MLEV pattern of $90_x 180_y 90_x$ composite refocusing pulses. In the preferred embodiment, all pulses are rectangular and non-selective with $$\frac{\gamma B_1}{2\pi} = 616 \text{ Hz}.$$

When using composite refocusing pulses, methods are used to compensate for $T_1$ signal decay effects during each refocusing pulse. Solutions include decreasing the pulse duration, increasing the refocusing interval, and using post-processing methods. The preferred embodiment uses a simple shift of echo times to account for $T_1$ signal decay effects without constraining the pulse duration or the refocusing interval. This correction is described in the publication by W. Foltz, et al., "$T_2$ Accuracy On A Whole-body Imager," MRM 38:759–768 (1997).

The effects of RF field offsets on the $90_x/90_{-x}$ excitation/tip-up pulse pair is addressed by using phase-cycling methods which subtract out the $T_1$ bias or by using composite 90° excitation and tip-up pulses which ensure an efficient manipulation of magnetization between the transverse plane and the longitudinal axis. The preferred embodiment uses a $360_x 270_x 90_y$ pulse for excitation and a $45_{-x} 90_{-y} 90_{-x} 45_y$ pulse for tip-up. This pulse combination provides dual RF and static field insensitivity without increasing the imaging time. In the preferred embodiment, both pulses are rectangular and non-selective with $$\frac{\gamma B_1}{2\pi} = 616 \text{ Hz}.$$

Following the preparation interval, $T_2$ contrast is stored temporarily along the longitudinal axis. During this time, the $T_2$-weighting will degrade gradually by $T_1$ relaxation effects. Methods which remove the additive $T_1$ recovery term will preserve the prepared $T_2$ contrast. The preferred embodiment cycles the longitudinally-stored $T_2$ contrast between the $\pm z$ axes by applying a robust inversion pulse immediately following the tip-up pulse on subsequent excitation. The additive term is removed upon subtraction of the acquired data. When using a series of small-tip angle excitations, the sensitivity to subtraction errors can be reduced by applying an inversion pulse following each small-tip angle excitation.

To perform MR oximetry within small and centrally-located vessels, such as coronary veins the oximetry MR pulse sequence must have improved sensitivity. Due to the strong dependence of the oxygen effect on $\tau_{180}$, careful selection of this parameter is an important aspect of the oximetry protocol. In the large vessel studies, where oxygen saturations are high (% $O_2 \geq 70\%$), $\tau_{180}$ is set to 24 ms to maximize the measurement's sensitivity to small changes in % $O_2$. In small and centrally located vessels which have low oxygenation such as the coronary veins (% $O_2 \sim 30\%$), the setting of $\tau_{180}$ to 24 ms is suboptimal due to a considerable shortening of $T_2$ ($T_2 \sim 50$ ms) and a lack of measurement sensitivity to % $O_2 \geq 50\%$. The preferred embodiment uses a much shorter $\tau_{180}$ of 6 ms to increase the vessel $T_2$ ($\sim 100$ ms). This provides two benefits; it increases the measurement's sensitivity to % $O_2 < 50\%$ and it improves muscle signal suppression by allowing for later echo times. The improved signal suppression is particularly important for measurements within vessels in and around the myocardium.

Figure 3:
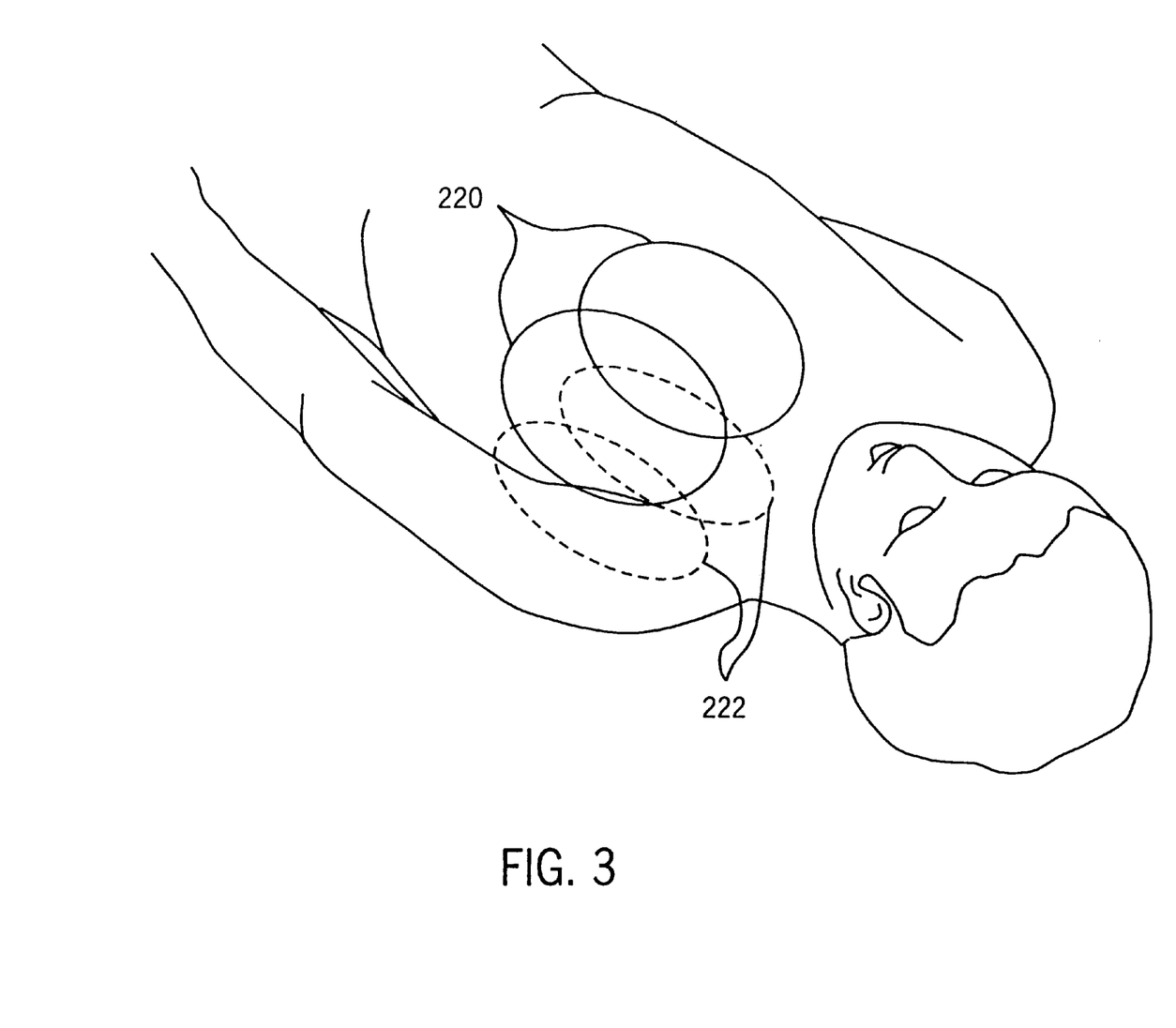
FIG. 3 is a pictorial representation of the preferred phase array coil used during the data acquisition.

A signal-to-noise ratio per pixel greater than 10 at the time of the longest $T_2$ preparation interval is essential to avoid noise bias in the $T_2$ measurement. In the large vessels, which are closer to the body surface, this SNR is achieved easily using a conventional 5 inch surface coil. Due to the rapid drop-off of sensitivity with depth when using such a coil, the SNR/pixel may be prohibitively low for measurements in small and centrally located vessels, such as those in and around the heart. As shown in FIG. 3, the solution to this problem is to use an array of local coils to receive the MR signal. Good visualization of a vessel for an oximetry measurement requires adequate spatial resolution and an imaging slice which is perpendicular to the vessel wall. This is straightforward for measurements in large vessels with little motion. Measurements within smaller vessels which move considerably, such as those in and around the heart, pose a greater challenge for reliable visualization. Spatial resolution can be increased by sampling higher spatial frequencies during the data acquisition. The preferred method is to place at least 6 pixels across the vessel diameter. For the coronary sinus, the primary draining vein of the heart, this requires an in-plane resolution of approximately 1.5 mm by 1.5 mm. Measurements in smaller vessels require higher in-plane resolution. In a practical $T_2$ measurement, in-plane resolution is limited by the direct proportionality between resolution and the SNR/pixel, thus necessitating a trade-off.

The prescription of a slice which is perpendicular to the wall of a moving vessel requires prior knowledge of the vessel's orientation in both time and space. The preferred method uses the respiratory compensation and cardiac gating schemes and the graphic prescription options available on the GE Signa MR system to acquire a localizer image. In the preferred embodiment described below, axial $T_1$-weighted spin echo images are acquired as localizers with the blood signal nulled using the commercially available in-flow saturation option on the GE Signal MR System.

DESCRIPTION OF THE PREFERRED EMBODIMENT

Figure 1:
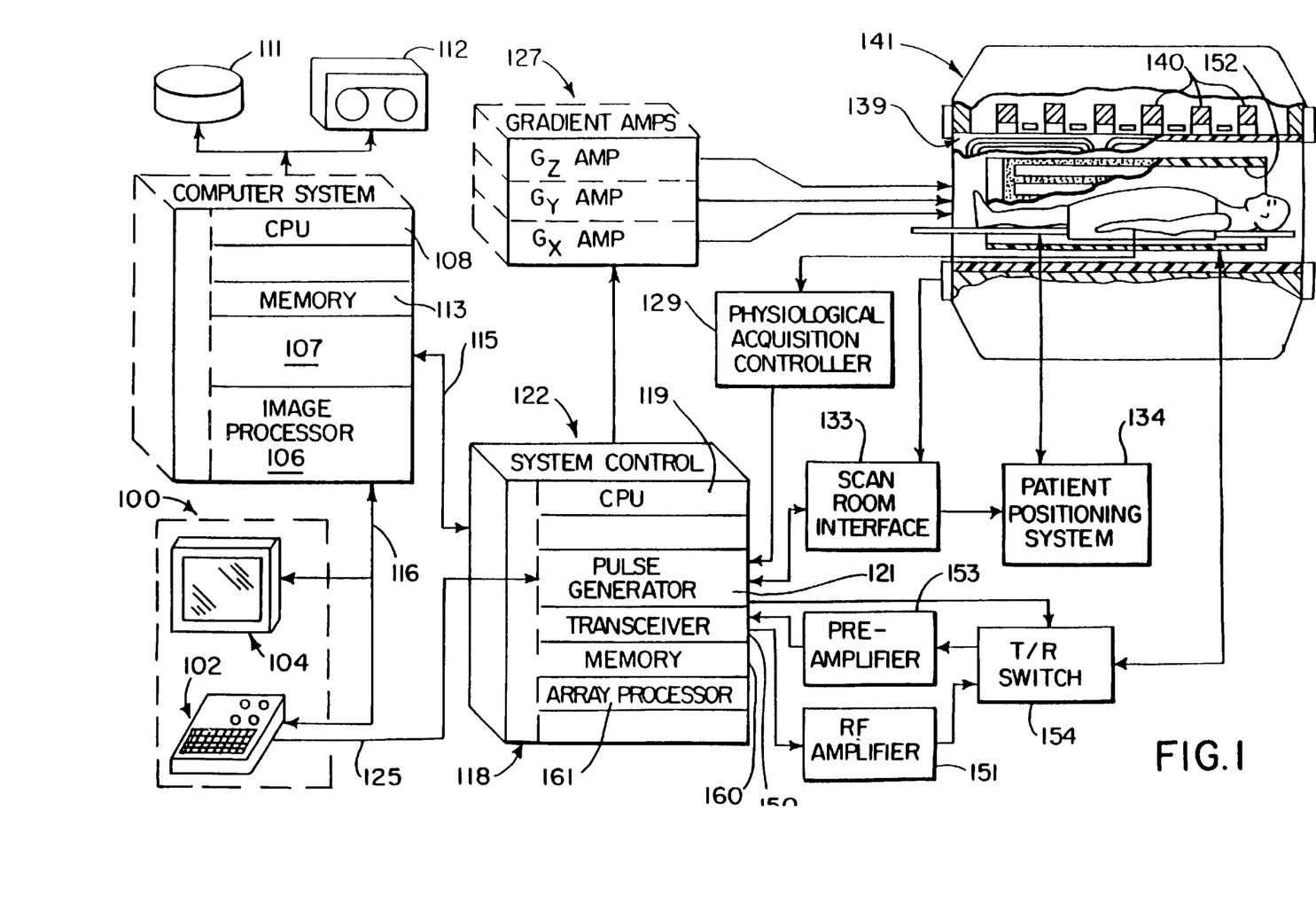
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan.

The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a four channel preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. As will be described in more detail below, the transmit/receive switch 154 also enables a separate, four coil, phased-array surface coil to be used in the receive mode.

The NMR signals picked up by the RF surface coil are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

For a more detailed description of the transceiver 150, reference is made to U.S. Patent Nos. 4,952,877 and 4,992,736 which are incorporated herein by reference.

Figure 2:
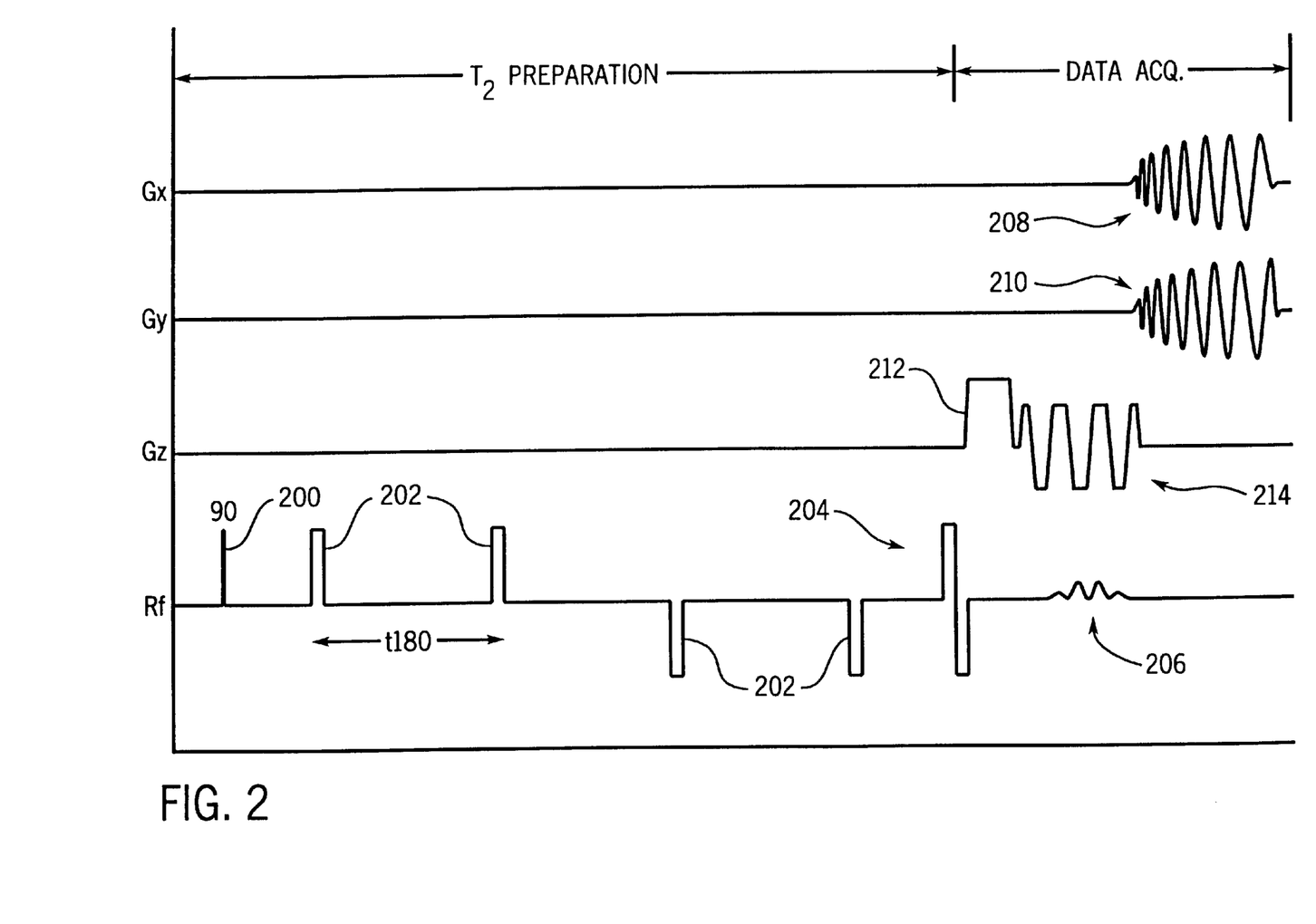
FIG. 2 is a graphic representation of the preferred pulse sequence used to acquire MR oximetry data.

Referring particularly to FIG. 2, the pulse sequence employed in the preferred embodiment includes a $T_2$ preparatory segment and an imaging segment. The $T_2$ preparation segment is designed to store $T_2$-weighted magnetization along $M_z$ in a manner that is robust in the presence of flow as well as $B_0$ and $B_1$ inhomogeneities. A $90_x°$ RF excitation pulse 200 is followed by a train of $180_y°$ RF refocusing pulses 202, which are equally separated by an interval τ180. At the echo of the final refocusing pulse 202, the $T_2$-weighted transverse magnetization is returned to the longitudinal axis by an RF pulse 204. As described in the above-cited U.S. Pat. No. 5,233,991, $T_2$ is measured by a series of acquisitions in which the time interval of the $T_2$ preparatory segment is set to different values by changing the number of RF refocusing pulses 202 used.

To minimize flow-sensitivity, the entire $T_2$ preparatory segment is nonselective. Thus, there are no gradients applied and no gradient moments to be nulled. In addition, the regular refocusing achieved by the train of $180_y°$ pulses 202 lessens the amount of dephasing due to flow through susceptibility gradients. Assuming ideal RF homogeneity, phase accrued by spins moving at a constant velocity through local $B_0$ inhomogeneities will be refocused on each even echo if the $B_0$ inhomogeneity can be modeled as a linear gradient. The validity of such a model improves as $\tau 180$ interval decreases because spins travel a shorter distance between pulses.

Ideally, the $180_y°$ RF refocusing pulses 202 perfectly refocus the transverse magnetization generated by the initial $90_x°$ RF excitation pulse 200 and invert any longitudinal magnetization. However, errors in the refocusing train due to $B_0$ and $B_1$ inhomogeneity can excite spurious signals. Two compensation schemes are used to minimize these errors. First, the $180_y°$ pulses 202 are weighted in an MLEV pattern. This method modulates the sign of the RF refocusing pulse 202 in a manner which compensates for pulse imperfections and yields superior refocusing following $2^n$ pulses where n is an integer. The second method involves the use of composite $180_x°$ refocusing pulses. These $90_x°$ $180_y°$ $90_x°$ pulses provide second-order correction to errors in $B_1$ amplitude and provide accurate inversion of any longitudinal magnetization. The use of these two compensation strategies yields a dramatic reduction in spurious signals. All RF pulses used in the $T_2$ preparatory segment are rectangular with minimum width and maximum amplitude (a 90° excitation=406 $\mu$s for the preferred hardware).

A $-90_x°$ RF pulse 204 is the intuitive choice to return the $T_2$-weighted magnetization to the longitudinal axis at the end of the preparatory segment. However, the performance of a $T_2$ preparatory segment using this pulse is sensitive to $B_0B_1$ inhomogeneity. Instead, a composite $45_{-x}°$ $90_y°$ $90_{-x}°$ $45_y°$ RF pulse 204 is utilized for tip-up combined with a $360_x°$ $270_{-x}°$ $90_y°$ excitation at the beginning of the preparatory segment.

The oxygen effect on blood's $T_2$ depends strongly on the refocusing interval ($\tau 180$). Using a refocusing interval of 24 ms results in a short $T_2$ for sinus blood (~50 ms). The preferred embodiment uses a much shorter refocusing interval ($\tau 180$) of 6 ms to increase coronary sinus $T_2$ ($T_2$~110 ms). This provides two benefits; it increases the measurement's sensitivity to % $O_2$ for values <50% and it improves myocardial signal suppression by allowing for later echo times.

A single-slice image data acquisition segment is used in the preferred embodiment. Each TR, the preparatory segment is followed by a spatial-spectral RF excitation 206 and the acquisition of one spiral interleaf during the application of two sinusoidal, in plane readout gradients 208 and 210. Because the spatial-spectral RF pulse 206 selectively excites water while isolating the slice of interest, this sequence rejects lipids, Furthermore, the spiral acquisition has excellent flow properties which are well-suited to coronary imaging. A spoiler gradient pulse 212 separates the $T_2$ preparatory segment from the data acquisition segment, and it is applied along the slice select axis just prior to a set of slice select gradient pulses 214.

Good visualization of a coronary vein for an oximetry measurement requires adequate spatial resolution and an imaging slice which is perpendicular to the vessel wall. Spatial resolution can be increased by sampling higher spatial frequencies during the data acquisition. The preferred method is to place 6 pixels across the vessel diameter. For the coronary sinus, this requires an in-plane resolution of approximately 1.5 mm×1.5 mm. The prescription of a slice which is perpendicular to the vessel wall requires prior knowledge of the vessel orientation. The preferred method uses the localizer image and the graphic prescription option available on the GE Signa MR system to accomplish this.

Other data acquisition sequences can be used with the $T_2$ preparatory segment. Indeed, it is one of the advantages of the $T_2$ preparatory segment that it can be used with a variety of spatially localized data acquisition techniques. For example, a series of small-tip angle excitations can be applied following the tip-up RF pulse 204. By imaging different slices or different lines of k-space following each excitation, one can measure $T_2$ in single-slices, multiple slices, or in three dimensions more rapidly. Note that the choice of small-tip angle excitation pulse is flexible and can include either a spectral-spatial pulse or a flow-robust half-pulse.

To ensure the magnetization-prepared $T_2$ measurement is accurate in vivo, several improvements have been made to deal with the particular application in the coronary vasculature. These improvements address issues associated with robustness, the preservation of $T_2$ contrast during the period of longitudinal storage, compensation for respiratory motion, compensation for cardiac motion, and compensation for heart rate variations. Each improvement will now be discussed.

On a whole-body imager, $T_2$ measurement accuracy is degraded by errors in the refocusing RF pulse train and in the $90_x/90_{-x}$ excitation/tip-up pulse pair associated with the imager's practical limitations to RF amplitude $$\left(\frac{\gamma B_1}{2\pi} < 1 \text{ kHz}\right)$$

and refocusing interval ($\tau_{180}$>5 ms) and inherent field inhomogeneities ($\Delta B_1$ tends to be within 15–20%, $\Delta B_0$ tends to be well within 1.5 ppm). The preferred method relies on robust RF pulses, phase-cycling schemes, and simple post-processing methods to ensure accurate $T_2$ contrast development in a simple yet effective manner. On a whole-body imager, the effects of RF and static field inhomogeneities during the refocusing RF pulse train are addressed using trains of relatively simple composite RF refocusing pulses 202 with good RF cycling patterns. The preferred embodiment uses a MLEV pattern of $90_x 180_y 90_x$ composite refocusing pulses.

$T_2$ measurements in and around the heart are inherently sensitive to respiratory motion due to the relatively long data acquisition times. If not compensated for, blurring and motion artifacts will degrade the quality of each $T_2$-weighted image. A number of respiratory compensation methods exist which can improve image quality. Schemes which rely on breath-holding, rapid imaging, or motion monitoring and re-acquisition methods attempt to reduce the number of respiratory phases in the acquired data. Other methods rely on the periodicity of the respiratory cycle to implement post-processing corrections.

The preferred embodiment uses a respiratory bellows and the signal processing unit of the MR imager to monitor and record the respiratory phase at the time of each data acquisition. Following the collection of a full data set, a histogram of the respiratory phases is constructed. Overscanning and the well-known Diminishing Variance Algorithm are then applied to "freeze" the respiratory motion.

If not compensated, cardiac motion can introduce considerable artifacts and blurring into a $T_2$-weighted image.

Methods to "freeze" heart motion rely on prospective gating using a plethysmograph placed on a finger for an ECG trigger. Due to the considerable delay between the R wave and the triggering of the plethysmograph, the preferred embodiment uses the R wave of the ECG signal for triggering the pulse sequence of FIG. 2.

Because the acquisition of $T_2$-weighted images in and around the heart requires multiple data acquisitions, a steady-state longitudinal magnetization is desirable at the time of each excitation. For vascular $T_2$ measurements, a steady-state magnetization is difficult to achieve due to variability in the heart rate. The simplest method to reduce the effects of heart rate variability on the $T_2$ measurement is to allow more than one heart beat for $T_1$ recovery. Other methods control the duration of $T_1$ recovery by nulling the longitudinal magnetization at a set time before each excitation pulse. In the preferred embodiment, this problem is addressed by acquiring data following every other heart beat.

A signal-to-noise ratio (SNR) greater than 10 at the time of the longest $T_2$ preparation interval is essential to avoid noise bias in the $T_2$ measurement. However, the coronary veins of primary clinical interest are located outside of the sensitive region of conventional surface coils and the SNR/pixel may be prohibitively low when using these coils. As shown in FIG. 3, the solution to this problem is to use local coils to receive the NMR signals. A four coil phase array coil such as that described by P. A. Bottomley et al, in *"What is the Optimum Phased Array Coil Design for Cardiac and Torso Magnetic Resonance,"* MRM 37:591–599 (1997) is used. To maximize sensitivity to the deep coronary veins, this coil is implemented as two dual coil arrays 220 and 222 with one placed on the chest and the other placed behind the back of the supine subject. Using this design, we observe a 2.7-fold improvement in coronary sinus SNR relative to the MRI system body coil 152.

The determination of flow and oxygen consumption using oximetry relies on the Fick principle. The Fick principle for oximetry is set forth in Eq. 1. It states that flow (Q) through a region is proportional to the rate of oxygen consumption within the region relative to the change in blood oxygen saturation across that region.

$$Q \text{ (L/min)} = \frac{\text{rate of oxygen consumption (ml/min)}}{((\% \ O_{2,art} - \% \ O_{2,ven}) * [Hb]) \text{ (ml/L)}} \quad (1)$$

Hence, with independent knowledge of the oximetry information and one other variable, either flow or the rate of $O_2$ consumption, the other variable can be calculated. If measures of oxygen consumption rate are desired, coronary flow can be calculated using thermodilution following catheterization or using flow-sensitive imaging methods. The preferred method is to use phase-contrast MR imaging methods such as that disclosed in U.S. Pat. No. Re. 32,701 which is incorporated herein by reference. Coronary arterial % $O_2$ can be calculated using oximetry methods in the periphery. The preferred method is to use an optical pulsed oximetry method. The preferred method for measuring venous% $O_2$ is to use measurements of $T_2$ in the coronary sinus vein which drains the left ventricular myocardium. This measurement can be used to evaluate the left ventricular function.

Coronary Flow Reserve

Based on Eq. 1, coronary flow may be calculated with knowledge of arterial and venous % $O_2$ and the rate of myocardial oxygen consumption. Repetition of each measurement before and after stress is applied provides a measure of basal and peak coronary flow. If the perfusion pressure is held constant, the ratio of these two measured flows is the coronary flow reserve. Stress may be applied through exercise or via a drug injection. Possible drugs include dipyridamole, adenosine, or dobutamine. Due to its efficacy and the duration of its effects (~30 minutes), the preferred method is to apply stress by injecting dipyridamole.

The preferred method for calculation of coronary flow reserve uses measurements of coronary sinus $T_2$ before and after an injection of dipyridamole. As coronary arterial % $O_2$ measurements are insensitive to stress, they need not be repeated. Due to the absence of practical measurement techniques, estimates for the basal and peak myocardial oxygen consumption rates are currently taken from the literature.

Figure 4:
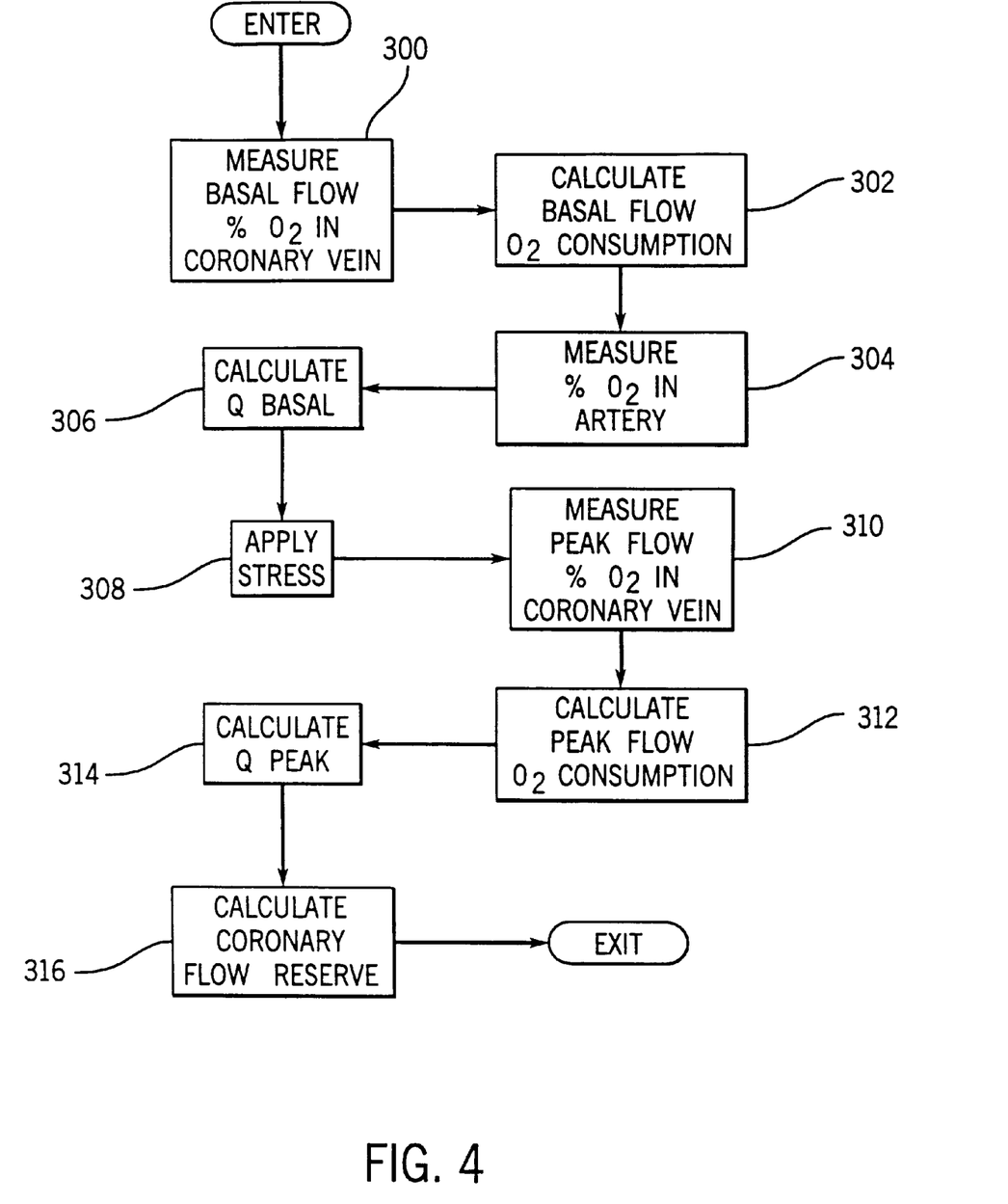
FIG. 4 is a flow chart of a preferred method for measuring coronary flow reserve.

FIG. 4 is a flow chart of the steps necessary to practice this method of calculating coronary flow reserve. The first step is to measure the % $O_2$ in the coronary vein as indicated at process block 300. This is accomplished using the pulse sequence of FIG. 2 in the MRI system of FIG. 1 in accordance with the oximetry method described in the above-cited U.S. Pat. No. 5,233,991 and the Wright et al publication *"Estimating Oxygen Saturation of Blood in Vivo with MR Imaging at 1.5T"*. The coronary $O_2$ consumption at the basal flow rate is then calculated as indicated at process block 302.

As indicated at process block 304, the next step is to measure % $O_2$ in the arteries. This is accomplished using the optical pulsed oximetry method described above, and it need only be done once during the procedure. This is followed by calculating $Q_{BASAL}$ at process block 306 in accordance with the following equation (2).

$$Q_{basal} \text{ (L/min)} = \frac{\text{rate of } O_2 \text{ consumption (ml/min)}}{((\% \ O_{2,art} - \% \ O_{2,ven,basal}) * [Hb]) \text{ (ml/L)}} \quad (2)$$

Where [Hb] is the concentration of hemoglobin in blood, determined from a bloodtest. A stress is then applied to the subject as indicated at 308 and the % $O_2$ in the coronary vein is measured at process block 310. This is the exact same procedure described above for process block 300, but it measures % $O_2$ at peak blood flow while the subject is under coronary stress. The coronary $O_2$ consumption at peak flow is then calculated at process block 312 using the same method as that described above for process block 302. From these measurements the value of $Q_{PEAK}$ is calculated at process block 314 in accordance with the following equation (3):

$$Q_{peak} \text{ (L/min)} = \frac{\text{rate of } O_2 \text{ consumption (ml/min)}}{((\% \ O_{2,art} - \% \ O_{2,ven,peak}) * [Hb]) \text{ (ml/L)}} \quad (3)$$

The coronary flow reserve is then calculated at process block 316 in accordance with the following equation (4):

$$CFR = \frac{Q_{peak}}{Q_{basal}} = \frac{\text{rate of } O_2 \text{ consumption with } Q_{peak}}{\text{rate of } O_2 \text{ consumption with } Q_{basal}} * \frac{(\% \ O_{2,art} - \% \ O_{2,ven,basal})}{(\% \ O_{2,art} - \% \ O_{2,ven,peak})} \quad (4)$$

Based on equation 1, the rate of myocardial oxygen consumption may also be determined with knowledge of arterial and venous % $O_2$ and the coronary flow. Peak and basal consumption rates can be calculated using measurements before and after stress. The preferred method, for calculation of the rate of myocardial oxygen consumption uses measurements of coronary sinus $T_2$ before and after an injection of dipyridamole. Because coronary arterial % $O_2$ measurements are insensitive to stress, they need not be repeated. Coronary venous flow is measured using phase-contrast MRI methods.

Figure 5:
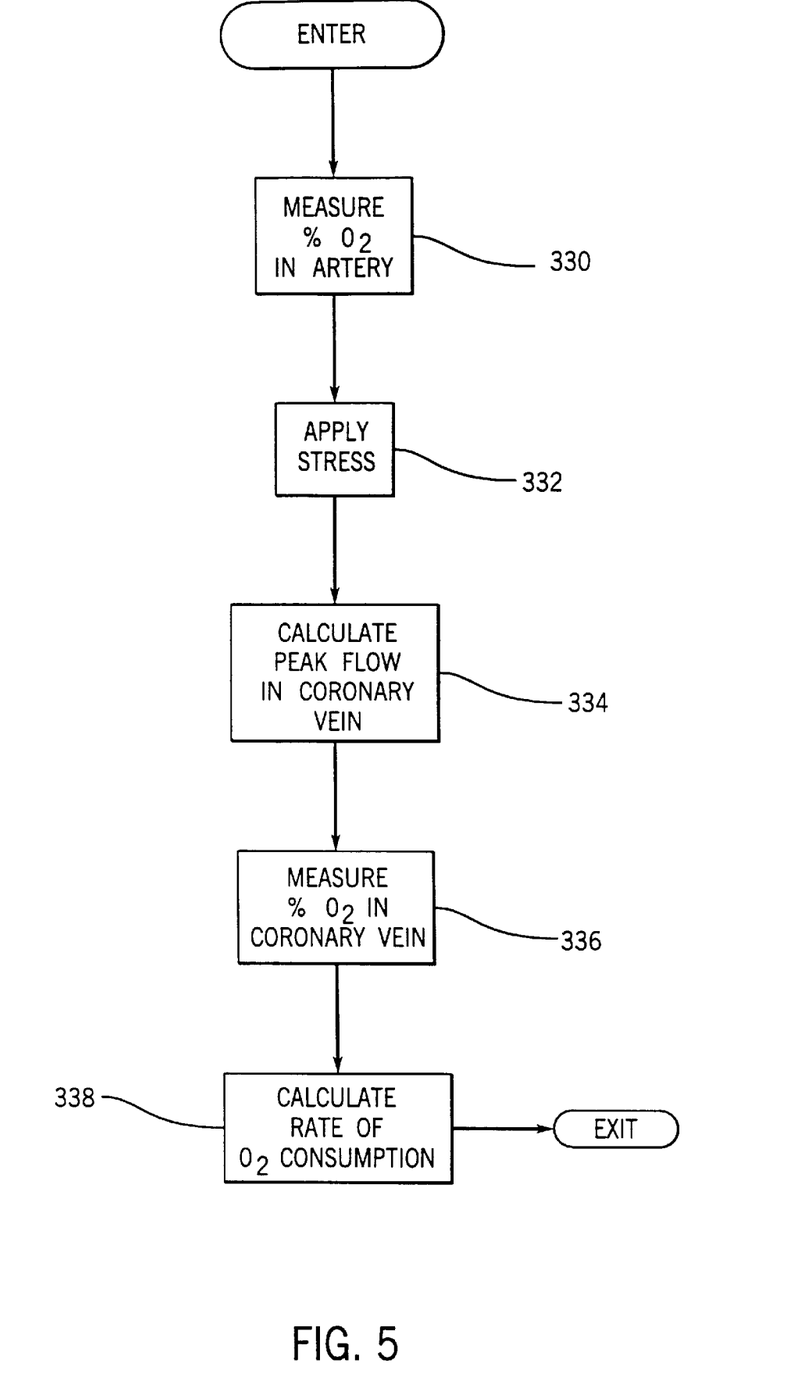
FIG. 5 is a flow chart of a preferred method for measuring coronary oxygen consumption.

FIG. 5 is a flow chart of the steps necessary to practice this method of calculating myocardial oxygen consumption. The first step is to measure % $O_2$ in a peripheral artery as indicated at process block 330. This is accomplished using the optical pulsed oximetry method described above. Stress is then applied to the subject as indicated at 332 and the peak flow in the sinus vein is then calculated at process block 334. The % $O_2$ in the sinus vein is then measured at process block 336 using the pulse sequence of FIG. 2 in the MRI system of FIG. 1. The oximetry method described in the above-cited U.S. Pat. No. 5,233,991 is used for this purpose. As indicated at process block 338, the last step in the method is to calculate the $O_2$ consumption rate in accordance with the following equation (5):

$$\text{rate of } O_2 \text{ consumption (ml/min)} = \frac{Q \text{ (L/min)}}{((\% O_{2,art} - \% O_{2,ven}) * [Hb]) \text{ (ml/L)}} \quad (5)$$

It is claimed:

1. A method for measuring coronary flow reserve, the steps comprising:

a) calculating the percentage of oxygenated blood (% $O_2$) flowing through a coronary vein in a subject by measuring the $T_2$ time constant thereof using an MR imaging system which repeatedly executes a pulse sequence comprised of a $T_2$ preparatory segment and an image data acquisition segment;

b) calculating the oxygen consumption of the myocardium in the subject;

c) measuring the percentage of oxygenated hemoglobin in blood (% $O_2$) flowing through an artery in the subject;

d) calculating basal coronary flow ($Q_{BASAL}$) using the values obtained in the steps a), b) and c);

e) applying a stress to the subject to produce a high coronary blood flow;

f) repeating step a) to produce a value indicating the percentage of oxygenated blood (% $O_2$) flowing through said coronary vein;

g) calculating the oxygen consumption of the myocardium in the subject;

h) calculating the peak coronary flow ($Q_{PEAK}$) using the values obtained in steps c), f) and g); and i) calculating the coronary flow reserve of the subject using the values of $Q_{BASAL}$ and $Q_{PEAK}$.

2. The method as recited in claim 1 in which the $T_2$ preparatory segment of said pulse sequence includes:

producing an RF excitation pulse which produces transverse magnetization in the blood flowing in said coronary vein;

producing a plurality of RF refocusing pulses; and producing a second RF excitation pulse which tips the transverse magnetization back to a longitudinal axis prior to the execution of the image data acquisition segment of the pulse sequence.

3. The method as recited in claim 1 in which step a) is performed using an array of local coils having at least one coil disposed on the chest of the subject and at least one coil disposed on the back of the subject.

4. The method as recited in claim 3 in which there are two coils disposed on the chest and two coils disposed on the back of the subject.

5. A method for performing MR oximetry in an MR system, the steps comprising:

a) performing a pulse sequence with the MR system to acquire $T_2$-weighted image data from which an image may be reconstructed;

b) measuring the $T_2$ of blood in a region of interest by performing step a) a plurality of times; and c) calculate the blood oxygen saturation using the measured $T_2$;

wherein the pulse sequence includes an image data acquisition segment preceded by a $T_2$ preparatory segment, and the $T_2$ preparatory segment includes:

generating an RF excitation pulse that tips longitudinal magnetization in the region of interest to produce transverse magnetization;

generating one or more RF refocusing pulses at equal intervals following the RF excitation pulse; and generating a second RF excitation pulse at said interval following the last RF refocusing pulse to tip transverse magnetization back to the longitudinal axis prior to the execution of the image data acquisition segment.

6. The method as recited in claim 5 in which said interval is less than 10 milliseconds.

7. The method as recited in claim 5 in which the region of interest is a coronary blood vessel and step a) is performed using an array of local coils to receive the $T_2$-weighted image data, one coil in the array of local coils being disposed on one side of the coronary blood vessel and a second coil in the array of local coils being disposed on the other side of the coronary blood vessel.

8. A method for measuring the myocardial oxygen consumption of a patient's heart, the steps comprising:

a) measuring the percentage of oxygenated blood (% $O_2$) flowing through an artery in the patient;

b) applying a stress to the subject to produce a high coronary blood flow;

c) determine the peak blood flow in the heart's sinus vein;

d) measure the percentage of oxygenated blood (% $O_2$) flowing through the sinus vein by measuring the $T_2$ time constant thereof using an MR imaging system which repeatedly executes a pulse sequence comprised of a $T_2$ preparatory segment and an image data acquisition segment; and e) calculate the rate of oxygen consumption using the information from steps a), c) and d).

* * * * *